United States Patent [19]

Weissenburger

[11] Patent Number: 4,552,266
[45] Date of Patent: Nov. 12, 1985

[54] DISPOSABLE DENTAL CAPSULE

[75] Inventor: Edward Weissenburger, Mercerville, N.J.

[73] Assignee: Johnson & Johnson, New Brunswick, N.J.

[21] Appl. No.: 41,756

[22] Filed: May 25, 1979

Related U.S. Application Data

[63] Continuation-in-part of Ser. No. 933,015, Aug. 14, 1978, abandoned.

[51] Int. Cl.[4] .............................................. B65D 81/32
[52] U.S. Cl. .................................... 206/220; 206/63.5
[58] Field of Search ............. 206/219, 220, 365, 63.5; 128/272

[56] References Cited

U.S. PATENT DOCUMENTS

| | | | |
|---|---|---|---|
| 2,549,417 | 4/1951 | Brown | 128/272 |
| 2,717,601 | 9/1955 | Brown | 128/272 |
| 2,794,437 | 6/1957 | Tash | 128/272 |
| 3,139,181 | 6/1964 | Kobernick | 206/63.5 |
| 3,149,717 | 9/1964 | Castelli | 206/365 |
| 4,185,740 | 1/1980 | Perfect | 206/220 |

Primary Examiner—William T. Dixson, Jr.
Attorney, Agent, or Firm—Charles J. Metz

[57] ABSTRACT

The reactive precursors of a dental amalgam are stored in separate chambers of a disposable dental capsule which allows the precursors to be mixed when desired with no special manipulation of the capsule by the user. The capsule comprises a closed cylindrical container divided into two noncummunicating, internal chambers by a movable, flexible disk. The dental capsule may contain mercury in one chamber and silver powder and a mixing pestle in the other chamber. When placed in a dental amalgamator, the mixing pestle drives the flexible disk to the end of the vessel of the container forcing the mercury to flow around the edges of the disk and to mix with the silver powder, thereby forming the dental amalgam.

18 Claims, 8 Drawing Figures

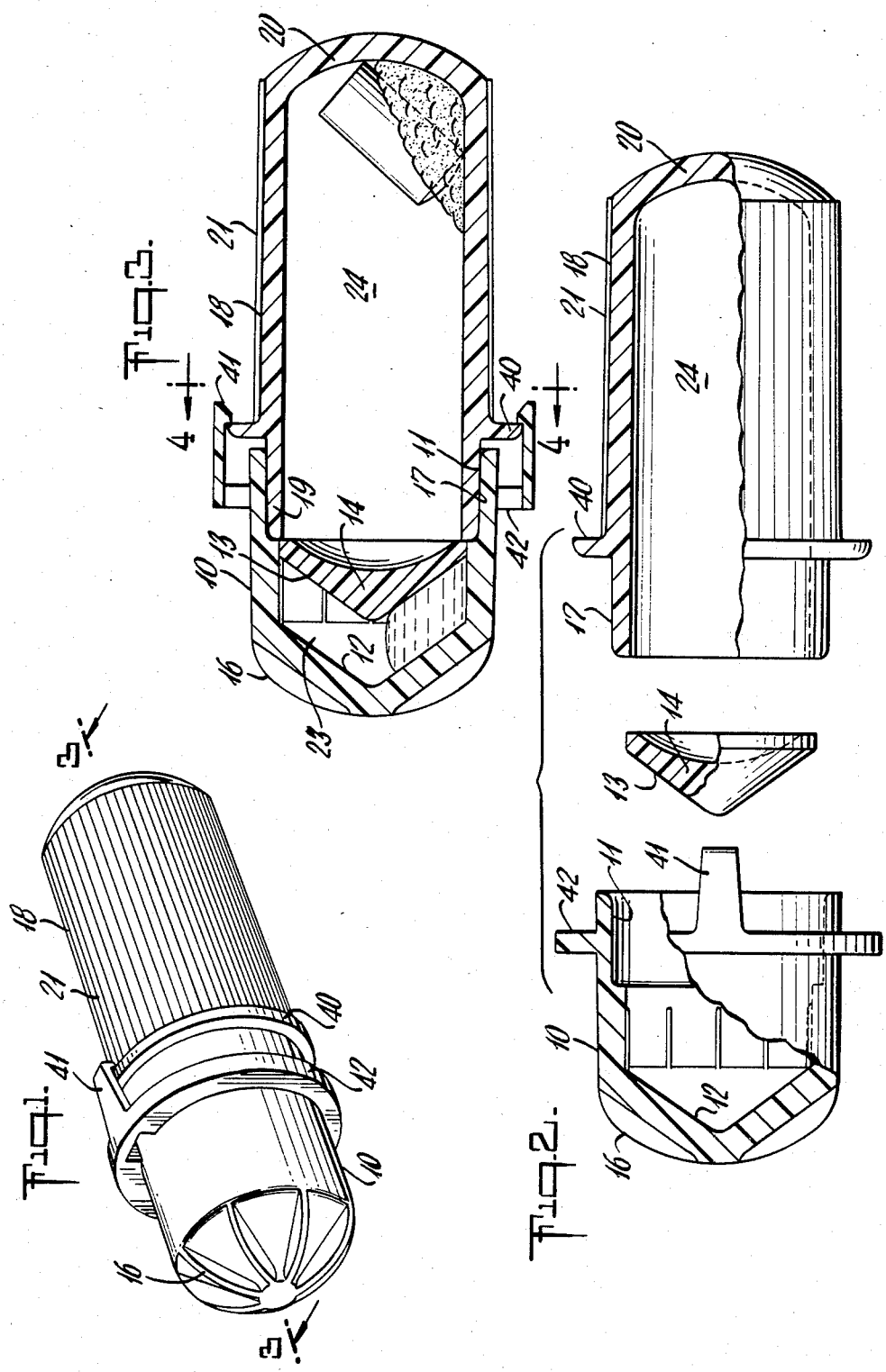

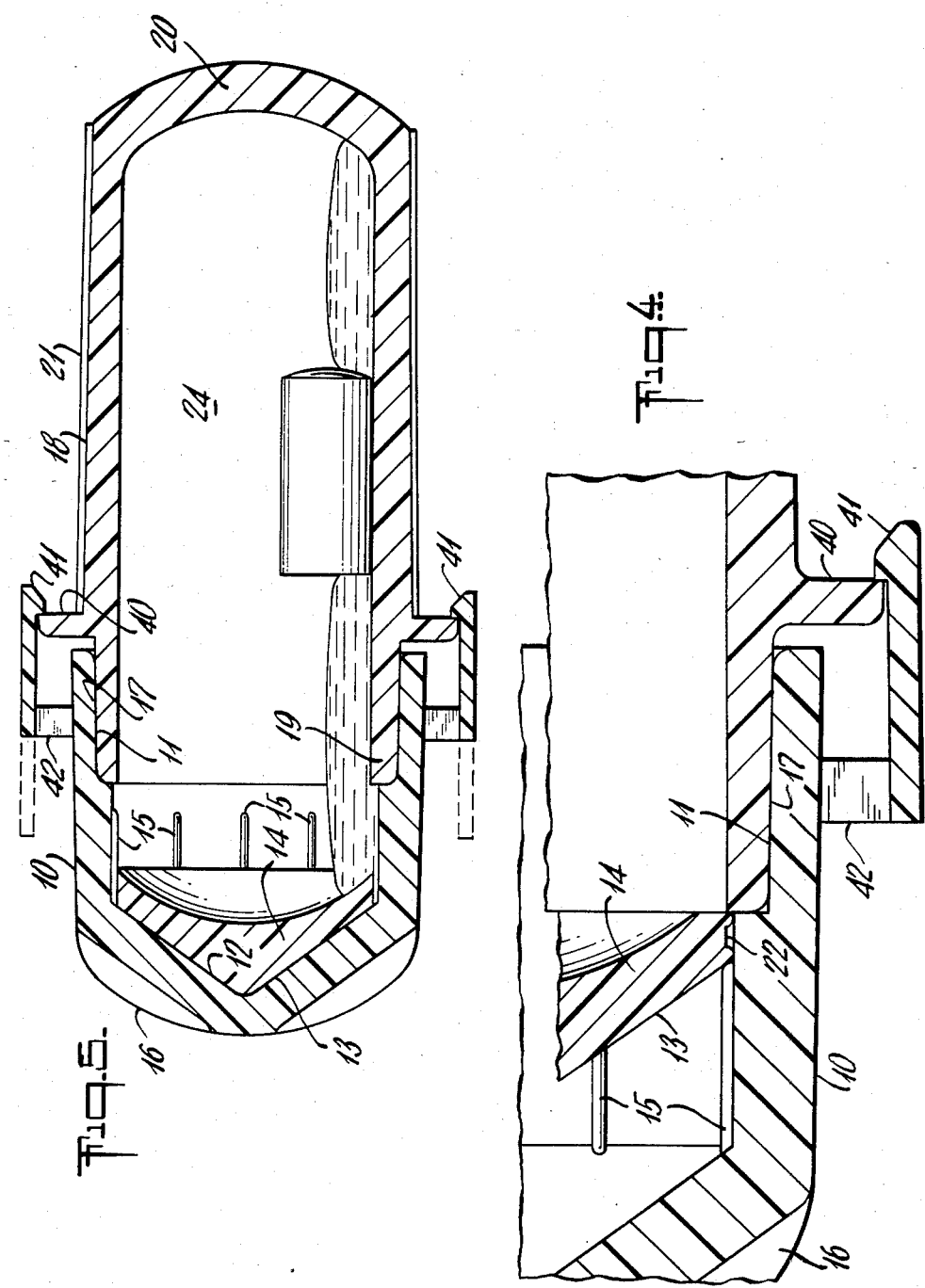

DISPOSABLE DENTAL CAPSULE

CROSS REFERENCE TO RELATED APPLICATIONS

The present application is a continuation-in-part of application Ser. No. 933,015, filed Aug. 14, 1978, now abandoned.

BACKGROUND OF THE INVENTION

The present invention relates to disposable capsules for prepackaging, storing and eventually mixing mercury and silver powder to form a dental amalgam.

Disposable capsules useful to maintain coreactive components such as dental amalgam precursors of mercury and silver or silver alloy are well-known. In all of the prior art disposable capsules, however, some manipulation of the capsule is required to effect mixing the coreactive components.

It would be very desirable to eliminate any such manipulation of the capsule and especially in the dental art it would be desirable to have a dental capsule containing the dental amalgam precursors from which a dental amalgam could be prepared merely by placing such capsule into an amalgamator.

Examples of prior art of disposable capsules include capsules having rupturable membranes and means for rupturing said membranes prior to mixing of coreactive components. For example, U.S. Pat. No. 3,451,540 teaches a disposable capsule comprising a telescoping cylinder which is activated by sliding the separate section together to rupture the membrane which divides the capsule into two chambers and thereby allows the coreactants maintained separate in such chambers to mix. Similar capsules are disclosed in U.S. Pat. Nos. 3,625,349 and 3,595,439 wherein the membrane is in the form of a pouch, containing a coreactant and such pouch is ruptured by either squeezing through a rotating mechanism or a sliding mechanism until it bursts. See also U.S. Pat. Nos. 3,907,106; 3,860,114; 3,841,467; 3,831,742, 3,655,035; 3,638,918; 3,756,571; and 1,774,258 for similar capsules.

Disposable capsules which utilize a removable plug to isolate the coreactive components and which plug is removed to allow such components to mix are also known in the art. See for example, U.S. Pat. No. 3,275,302, wherein a ball or a disk is positioned to divide the capsule into two chambers each containing a coreactive component. This capsule is activated by turning the capsule upside down to dislodge the ball or disk. See also U.S. Pat. Nos. 3,796,303; 3,809,225; 2,527,992; 2,527,991; and 3,785,481 for other capsules utilizing removable plugs.

Other disposable capsules employ a passageway between the two chambers which can be closed and opened by either twisting, sliding or unscrewing one or more sections of the capsule. For example, in U.S. Pat. No. 3,357,545 the top of the capsule is unscrewed to remove a stem on the upper section of said capsule from a conduit in the lower section. Removal of such stem allows the coreactive component maintained in the upper section to fall into the lower section. Also see U.S. Pat. Nos. 3,139,180; 3,139,181; 3,917,062; 3,963,120; and 3,924,741 for similar capsules.

It is accordingly an object of the present invention to provide a capsule for prepackaging and storing the precursors of dental amalgam, particularly mercury and silver or silver alloy. It is a further object of this invention to provide a dental capsule which allows the precursors to be mixed and the amalgam formed with no special manipulation of the dental capsule on the part of the user. It is yet a further object of this invention to provide a dental capsule which minimizes the possibility of mercury escaping into the environment either before or during the formation of the dental amalgam. These and other objects of the present invention will be apparent from the ensuing description and claims.

SUMMARY

The disposable dental capsules of the present invention comprise a closed cylindrical container divided into two, noncommunicating, internal chambers by a movable, flexible disk. A premeasured quantity of mercury is contained in one chamber, and a corresponding reactive amount of silver powder and a mixing pestle are contained in the other chamber. One face of the flexible disk is convex and contoured to conform to the shape of the opposing end of the chamber containing the mercury which is preferably cone shaped. When the capsule is placed in an amalgamator, the pestle drives the flexible disk to nest with the end of the container, forcing the mercury to flow around the edges of the disk and mix with the silver powder.

The capsules is conveniently composed of two, interlocking cylindric members, each having one closed end and one open end and including means for joining the open ends to form a closed container. The capsule also preferably includes internal means for locating and securing the flexible disk against inadvertent movement prior to use of the capsule to prevent premature mixing of the amalgam precursors. The capsule may also contain vanes or grooves in the wall of the mercury chamber to promote the flow of mercury around the disk when the capsule is placed in the amalgamator and the disk is driven to the end of the capsule.

The advantage of the dental capsule of the present invention resides in the fact that no manipulation of the capsule by the dentist or technician is required to effect mixing of the components. Since the capsule forms a closed container and there are no external moving parts, the possibility of mercury escaping into the environment is substantially eliminated.

After the amalgam has been formed inside the capsule, the cylindrical members are separated to remove the amalgamated composition. The two cylindrical members, one of which contains the flexible disk, and the pestle are then discarded.

DESCRIPTION OF DRAWINGS

FIG. 1 shows an external view of a capsule of the present invention.

FIG. 2 shows an exploded, partial, cross-sectional view of the capsule of FIG. 1.

FIG. 3 shows a cross-sectional view of the capsule of FIG. 1 prior to activation.

FIG. 4 shows in greater detail the relationship of the flexible disk and the assembly of the cylindrical sections of the capsule of FIG. 3.

FIG. 5 shows the capsule of FIG. 1 after activation and mixing of the coreactive components.

DESCRIPTION OF PREFERRED EMBODIMENTS

Figure 6:
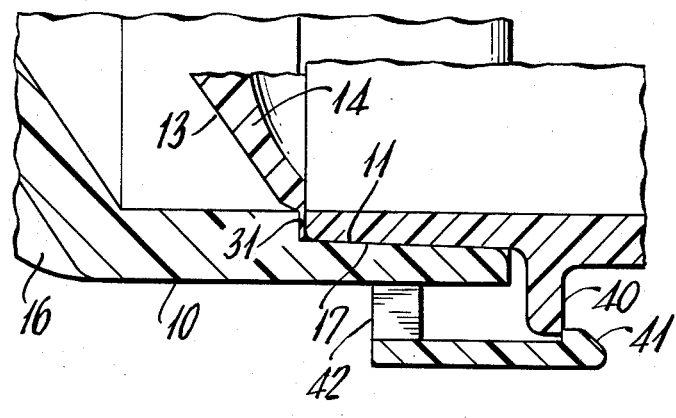
FIG. 6 shows a partial sectional view of the flexible disk and cylindrical sections in a second embodiment of the capsule.

Referring now to FIGS. 1–5, there is illustrated as a preferred embodiment of the present invention a disposable capsule comprising a first cylindrical section 10 having an open end 9 and conically-shaped closed end 12, a second cylindrical section 18 having an open end 19 and closed hemispherical end 20, and a flexible disk 14 which divides the assembled capsule into two non-communicating, internal chambers 23 and 24 as best seen in FIG. 3.

Flexible disk 14 is positioned in cylindrical section 10 with the edges of the disk engaging the walls of the section to form a continuous seal around the periphery thereof. Surface 13 of flexible disk 14 has a positive conical shape conforming to the negative conical shape of end 12 of cylindrical section 10 so that the disk nests with the cylinder end when forced against that end of the capsule.

The cylindrical section 10 also has an axially-extending groove 11 about its open end which allows cylindrical section 10 to telescopically engage open end 19 of cylindrical section 18, whereby a sealed capsule is formed when the first and second cylindrical sections are so engaged.

The wall thickness of cylindrical section 17 about the circumference of open end 19 is slightly greater than the depth of axially-extending groove 11 in cylindrical section 10 whereby when the cylindrical sections are telescopically engaged an axially-extending step 22 is provided in the interior of the capsule at the point where the two sections are joined.

Cylindrical section 10 includes a plurality of vanes 15 which extend along the wall thereof from the closed end toward the open end of the cylinder. In the illustrated embodiment, eight vanes are provided which are equidistantly oriented about the inner wall of the cylindrical section. It is desirable to have at least three vanes to keep the disk from cocking either during loading of the capsule or during activation as described below.

The dimensions of the vanes are selected to hold the flexible disk in a proper spaced relationship from the closed end of the cylindrical section without preventing the disk from nesting against such end when the capsule is activated. In a typical dental capsule having overall dimensions of from about 1 to $1\frac{1}{4}$ inches by approximately $\frac{1}{2}$ inch diameter, vanes 15 may protrude from the inner wall of the cylindrical section about 3 to 15 mils and be of 7 to 15 mils wide. The vanes may be tapered toward the open end of the cylinder to assist the disk in riding up on the vanes during mixing, provided, however, the angle must be sufficient to prevent dislocation of the disk during storage and shipping of the loaded dental capsules. It has been found that as the size and number of vanes are increased, more of the reactive component is retained in the capsule after mixing, and the skilled artisan will therefore choose dimensions for such vanes with a view toward securing the position of the disk during storage and shipping while minimizing the retention of residules in the capsule. As best illustrated in FIG. 4, the flexible disk 14 engages the inner wall of the capsule completely around the inner periphery of cylindrical section 10 and is held in place between vanes 15 and step 22 thus dividing the capsule into a first internal chamber 23 and a second internal chamber 24. The edge of the disk is preferably of a slightly greater thickness than the space between the step and the vanes to place the disk under light compression in the assembled capsule. In a typical dental capsule, such space may vary from about 5 to 60 mils and is typically about 30 mils.

In the illustrated embodiment, disk 14 has a conical surface extending into chamber 23 conforming to the conical shape of the opposing end of that chamber. The end of the chamber and the corresponding face of the disk may also be eliptical or hemispherical, but are preferably not flat since there would be a greater tendency to trap mercury between such flat surfaces during activation of the capsule.

Also as illustrated, chamber 23 contains mercury 25 and is appreciably smaller than chamber 24 which contains silver powder 27 and pestle 26. The precharged capsule may be activated by shaking in a dental amalgamator whereby the capsule is reciprocated in a direction along the major axis of the capsule. The pestle rebounds between the capsule end 20 and the opposing surface of the disk driving the disk quickly toward the closed end 12 of cylindrical section 10. As the disk moves into its nesting position against the surface of end 12, the mercury is hydrostatically forced to flow around the edges of the disk and into chamber 24. This flow of mercury is promoted by vanes 15 on the wall of section 10 which force openings in the seal around the edge of the disk. After a short time in the amalgamator the capsule has, in effect, only a single, large internal chamber of a volume substantially equal to the combined volumes of original chambers 23 and 24 and containing both the mercury and the silver.

The edge of the flexible disk, as previously noted, must seal against mercury leakage from chamber 23 during storage and shipping. In one embodiment illustrated in FIG. 4, the edge of the disk is grooved to provide a double seal line at the upper and lower surfaces of the disk to enhance its sealing capacity. Disk 14 is further provided with a concave face on the side facing the pestle which is believed to direct the force of the moving pestle uniformly across the disk thereby minimizing cocking as the disc rides up on the vanes and moves toward the closed end of cylindrical section 10.

The two cylindrical sections comprising the capsule of the present invention are provided with means to interlock the assembled capsule to insure the sections will not prematurely separate during shipping and handling. Referring now to FIG. 1, cylindrical section 18 is provided with axially-extending retainer flange 40 about the outer surface over which one or more lugs 41 integral with an axially-extending flange 42 on the outer surface of cylindrical section 10 snap fit. Flanges 40 and 42 are also useful in separating the hollow cylindrical sections. As shown in FIG. 5, the lugs 41 may be provided with extensions 43 beyond retainer flange 42 to provide a means for unsnapping said lugs by squeezing said extensions toward the body of the capsule.

In the illustrated embodiment of FIGS. 1–5, cylindrical section 10 has external ribs 16 radiating from the center of the closed end to conform the shape of the capsule to the shape of conventional amalgamator clips. The form shown in FIG. 1 is preferred because it maintains uniform wall thickness, and, hence, uniform cooling during molding of the capsule. Cylindrical section 18 is also provided with suitable friction-producing, gripping means about its external circumference such as the knurling 21 illustrated in FIG. 1 to assist in holding and opening the capsule after activation.

Figure 7:
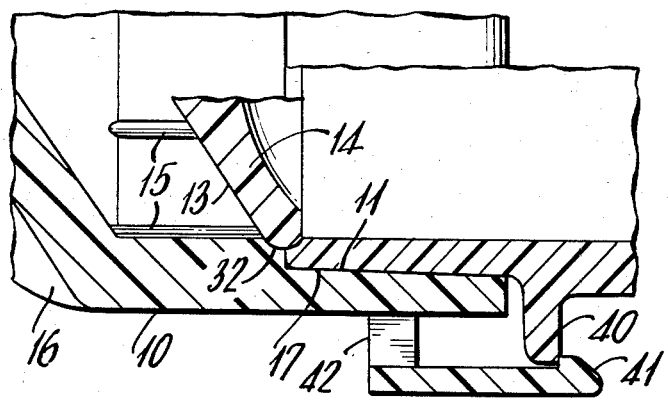
FIG. 7 shows a partial sectional view of the flexible disk and cylindrical sections in a third embodiment of the capsule.
Figure 8:
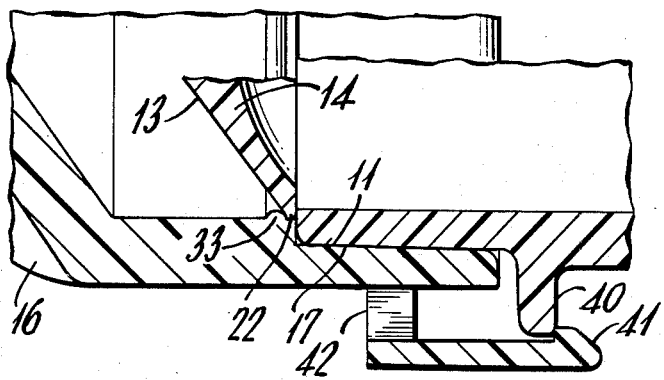
FIG. 8 shows a partial sectional view of the flexible disk and cylindrical sections in a fourth embodiment of the capsule.

Referring now to FIGS. 6-8, there are illustrated additional embodiments of the present invention wherein alternate means are utilized for locating and securing disk 14 within the capsule. In FIG. 6, disk 14 is provided with an annular flange 31 which extends into a space and is compressed between the base groove 11 in cylindrical section 10 and end 19 of cylindrical section 18. During activation of the capsule flange 31 is sheared or pulled free of the action of the pestle on disk 14, and the disk is released and driven to the end of cylindrical section 10. The side wall vanes illustrated in the previous figures are not required in the embodiment of FIG. 6 since the construction of the disk does not offer significant resistance to the flow of mercury around the edge of the disk once it has been freed from the annular flange.

Referring now to FIG. 7, there is illustrated another embodiment wherein disk 14 is located and secured in circumferential groove 32 formed in the wall of the capsule at the juncture of the two cylindrical sections. In a further embodiment illustrated in FIG. 8, disk 14 is located and secured between annular ridge 33 in cylindrical section 10 and lip 22 formed by end 19 of cylindrical section 18.

Those skilled in the art will appreciate that many other arrangements may be employed to locate and secure disk 14 within the capsule prior to activation. For example, the disk may be cemented to the wall of the capsule, or fused in place by induction bonding, or held in place by other mechanical means. The present application is accordingly not limited to any structural variation described herein.

The cylindrical sections of the capsule may be formed from any material which is inert to the coreactive components contained therein. In general, the cylindrical sections should be made of rigid material, such as metal, plastic, or the like, and in a preferred embodiment, they are made of rigid, thermoplastic material such as polycarbonate, polyacrylic, polyvinyl chloride, or the like. The material of choice for ease of fabrication is a polycarbonate such as LEXAN from General Electric Company or MERLON from Mobay Chemical Corporation; or an ABS polymer such as CYCOLAC ABS from Borg-Warner Corporation.

Disk 14 is preferably made of a resilient, flexible material such as, for example, acetal or polyester (e.g., DELRIN and HYTREL respectively, both being available from E. I. du Pont de Nemours & Co.), or the like thermoplastic materials. However, the material of choice is HYTREL.

The disk and the cylindrical sections are preferably formed by injection molding, but any suitable technique for forming the materials may be employed.

The use of rigid material for the hollow cylindrical sections minimizes retention of mercury in the capsule. Further, the combination of a rigid capsule and a flexible disk requires less strict manufacturing tolerances because the flexible material of the disk will adjust to minor deviations in the structure of the hollow cylindrical sections leading to more economic and efficient manufacture of the capsule of the invention.

To fill the dental capsule of the instant invention, a measured amount of silver alloy powder 27 or tablet of such powder is placed in cylindrical section 18 along with a mixing pestle 26 of sufficient weight to drive disk 14 back into cylindrical section 10 upon mixing. The proper amount of mercury to form dental amalgam with the silver powder is placed in cylindrical section 10, conveniently when it is positioned with the closed end downward. The flexible disk 14 is then placed in cylindrical section 10 and maintained in proper position by frictional engagement with the inner wall of the cylinder section or other suitable means. Cylindrical section 10 containing the mercury and the flexible disk 14 are then inverted and secured to cylindrical section 18 by means of lugs 41.

According to the invention, the premeasured components can be mixed without being touched or measured by the user in a more accurate and simple fashion than previously known. It should be understood that while the container of the invention has been exemplified in the mixing of dental amalgam, other dental compositions such as acrylate polymer dental filling materials may be packaged and mixed therein. Further, the container may be used in fields other than dentistry where a liquid component must be kept separate until just prior to use, as for example, in the prepackaging of epoxy resins and accelerators for the formation of cements.

What is claimed is:

1. A disposable dental capsule comprising:
   a first hollow cylindrical section having an open end and a closed end;
   a second hollow cylindrical section having an open end and a closed end;
   means for joining a securing said open ends of said first and second cylindrical sections to form a closed cylindrical container;
   a displaceable, flexible disk having an edge in sealing engagement with the inner wall of said cylindrical container whereby said container is divided into two, noncommunicating inner chambers, and having one face conforming to the shape of the inside surface of one end of said container; and
   edge compression means for maintaining said edge under compression to maintain the seal between said edge and said inner wall of said cylindrical container,
   whereby when said disk is displaced to said one end of said container, the face of said disk nests therewith and one of said inner chambers is substantially eliminated.

2. A capsule of claim 1 wherein the inside surface of said one end of said container is concave and the opposing face of said disk is convex.

3. A capsule of claim 2 wherein said face of said disk has a positive conical shape and said end of said container has a corresponding negative conical shape.

4. A capsule of claim 1 wherein said first hollow cylindrical section has an axially-extending internal groove about its open end telescopically engaging the open end of said second cylindrical section.

5. A capsule of claim 4 wherein said first and second cylindrical sections are secured in said telescopic engagement by means of lugs on said first section engaging a circumferential flange extending from said second section.

6. A capsule of claim 1 wherein said edge compression means includes said inner wall of said container having means for positioning and securing the edge of said flexible disk.

7. A capsule of claim 6 wherein said disk positioning and securing means comprises a circumferential groove in said wall receiving said edge of said disk.

8. A capsule of claim 6 wherein said disk positioning and securing means comprises circumferential ridges on said wall on either side of said edge of said disk.

9. A capsule of claim 6 wherein said disk positioning and securing means comprises a circumferential ridge on said one side of said edge of said disk, and a plurality of vanes circumferentially spaced around said wall and extending to the other side of said edge of said disk.

10. A capsule of claim 6 wherein said disk positioning and securing means comprises a circumferential groove in said wall between the juncture of said first and second cylindrical sections receiving an annular flange extending from the edge of said disk.

11. A capsule of claim 1 including a predetermined amount of mercury in the inner chamber defined by the face of the disk shaped to conform to the end of the container, a coreactive amount of silver in the other inner chamber, and a mixing pestle in the chamber containing the silver.

12. A disposable capsule comprising:
a first hollow cylindrical section having an open end and a closed end, said first section having an axially-extending internal groove about its open end and a plurality of vanes spaced from said groove and extending perpendicularly toward said closed end;
a second hollow cylindrical section having a closed end and an open end, said open end telescopically engaging said internal groove of said first section and being of sufficient thickness to provide an axially-extending step within said first section;
a flexible disk having one face engaging said axially-extending step and an edge engaging the walls of said first section at the space between said perpendicularly-extending vanes and said step, sid disk thereby dividing said capsule into two noncommunicating chambers; and
means for maintaining said edge under compression between said step and said perpendicularly-extending vanes; to thereby effect a seal between the said two noncommunicating chambers.

13. The capsule of claim 12 wherein the other face of said flexible disk is shaped to nest with the internal face of the closed end of said first cylindrical section.

14. The capsule of claim 13 wherein said face of said flexible disk has a positive conical shape, and the internal face of the closed end of said first cylindrical section has a corresponding negative conical shape.

15. The capsule of claim 12 wherein the edge of said flexible disk has a thickness of from 5 to 60 mils.

16. The capsule of claim 12 wherein said edge of said flexible disc is of a thickness greater than the space between said axially-extending step and said perpendicularly-extending vanes.

17. The capsule of claim 12 wherein said first and second cylindrical sections are each provided with interlocking means.

18. The capsule of claim 12 including a predetermined amount of mercury in the chamber of the second cylindrical section, a coreactive amount of silver in the chamber of the first cylindrical section, and a mixing pestle in the chamber containing the silver.

* * * * *